(12) United States Patent
Avery et al.

(10) Patent No.: US 11,670,405 B2
(45) Date of Patent: Jun. 6, 2023

(54) APPARATUS FOR CLINICAL DATA CAPTURE

(71) Applicant: Direct Supply, Inc., Milwaukee, WI (US)

(72) Inventors: William Avery, Brookfield, WI (US); Peter Klug, Bayside, WI (US); Kent Newbury, Fox Point, WI (US); Christopher Furmanski, Portola Valley, CA (US); Greg Georgatos, Rocklin, CA (US); Robert Laferriere, Menomonee Falls, WI (US)

(73) Assignee: Direct Supply, Inc., Milwaukee, WI (US)

( * ) Notice: Subject to any disclaimer, the term of this patent is extended or adjusted under 35 U.S.C. 154(b) by 649 days.

(21) Appl. No.: 16/508,866

(22) Filed: Jul. 11, 2019

(65) Prior Publication Data

US 2020/0020428 A1 Jan. 16, 2020

Related U.S. Application Data

(60) Provisional application No. 62/697,089, filed on Jul. 12, 2018.

(51) Int. Cl.
*G16H 10/60* (2018.01)
*G16H 15/00* (2018.01)
*G06F 16/9538* (2019.01)

(52) U.S. Cl.
CPC ......... *G16H 10/60* (2018.01); *G06F 16/9538* (2019.01); *G16H 15/00* (2018.01)

(58) Field of Classification Search
CPC ............................ G16H 10/60; G06F 16/9538
See application file for complete search history.

(56) References Cited

U.S. PATENT DOCUMENTS

| | | |
|---|---|---|
| 1,112,294 A | 9/1914 | Kepler |
| 6,544,174 B2 | 4/2003 | West et al. |
| 6,983,423 B2 | 1/2006 | Dvorak et al. |
| 7,383,196 B1 | 6/2008 | Tang et al. |
| 7,430,608 B2 | 9/2008 | Noonan et al. |
| 7,555,720 B2 | 6/2009 | O'Rourke |
| 7,895,527 B2 | 2/2011 | Zaleski et al. |
| 7,992,780 B2 | 8/2011 | Larsen |
| 8,451,314 B1 | 5/2013 | Cline et al. |
| 8,458,149 B2 | 6/2013 | Mudge |
| 8,543,999 B2 | 9/2013 | Dellostritto et al. |
| 8,565,500 B2 | 10/2013 | Neff |
| 8,732,795 B2 | 5/2014 | Skeel et al. |
| 8,907,782 B2 | 12/2014 | Baker et al. |
| 8,909,660 B2 | 12/2014 | Campbell et al. |
| 8,972,272 B1 | 3/2015 | Dvorak et al. |
| 9,077,533 B2 | 7/2015 | Oizumi et al. |
| 9,147,039 B2 | 9/2015 | Rana et al. |

(Continued)

OTHER PUBLICATIONS

International Search Report for International Application No. PCT/US2019/041616 dated Oct. 31, 2019.

*Primary Examiner* — John P Go
(74) *Attorney, Agent, or Firm* — Boyle Fredrickson, S.C.

(57) ABSTRACT

A clinical data interface device provides integrated portions of the electronic medical record system to identify and confirm a patient file for receiving data and personality modules for receiving and translating data from a variety of clinical device monitors for that identified patient.

22 Claims, 5 Drawing Sheets

(56) References Cited

U.S. PATENT DOCUMENTS

| | | | |
|---|---|---|---|
| 9,208,285 B1 | 12/2015 | Campbell et al. | |
| 9,218,455 B2 | 12/2015 | Neff | |
| 9,351,541 B2 | 5/2016 | Fennell | |
| 9,750,408 B1 | 9/2017 | Martin et al. | |
| 10,061,739 B2 | 8/2018 | Keegan et al. | |
| 10,181,011 B2 | 1/2019 | Dvorak et al. | |
| 2003/0144874 A1* | 7/2003 | Barret | G16H 40/67 705/2 |
| 2004/0102687 A1* | 5/2004 | Brashears | A61B 5/14551 600/323 |
| 2004/0153443 A1* | 8/2004 | McDonald | G16H 50/70 |
| 2005/0249239 A1 | 11/2005 | Pierce et al. | |
| 2005/0251423 A1 | 11/2005 | Bellam et al. | |
| 2005/0278001 A1* | 12/2005 | Qin | A61N 1/37247 607/67 |
| 2006/0117021 A1 | 6/2006 | Sidney et al. | |
| 2006/0155589 A1 | 7/2006 | Lane et al. | |
| 2007/0038402 A1* | 2/2007 | Zhang | H05K 9/00 702/117 |
| 2007/0185390 A1 | 8/2007 | Perkins et al. | |
| 2007/0294110 A1 | 12/2007 | Settimi | |
| 2008/0183502 A1* | 7/2008 | Dicks | G16H 40/67 705/2 |
| 2008/0263048 A1* | 10/2008 | Wise | G06Q 10/10 707/999.009 |
| 2008/0270912 A1* | 10/2008 | Booth | A61B 5/0002 715/748 |
| 2009/0069642 A1* | 3/2009 | Gao | H04L 67/125 600/300 |
| 2009/0177493 A1 | 7/2009 | Narayan | |
| 2010/0010320 A1 | 1/2010 | Perkins et al. | |
| 2010/0131298 A1 | 5/2010 | Buttner et al. | |
| 2011/0161112 A1* | 6/2011 | Keefe | G16H 40/67 705/3 |
| 2013/0157571 A1* | 6/2013 | Wondka | H04W 52/0245 455/41.2 |
| 2014/0114675 A1* | 4/2014 | Soon-Shiong | G16H 10/60 705/2 |
| 2014/0278536 A1* | 9/2014 | Zhang | G16H 10/60 705/3 |
| 2015/0269318 A1 | 9/2015 | Neff | |
| 2015/0347683 A1* | 12/2015 | Ansari | G16H 10/60 726/7 |
| 2016/0034642 A1 | 2/2016 | Ehrhart et al. | |
| 2016/0203283 A1 | 7/2016 | Baruah et al. | |
| 2017/0140134 A1 | 5/2017 | Brough et al. | |
| 2017/0193181 A1* | 7/2017 | Carter | G16H 40/67 |
| 2018/0032692 A1 | 2/2018 | Hickle et al. | |
| 2018/0270220 A1 | 9/2018 | Jensen et al. | |

* cited by examiner

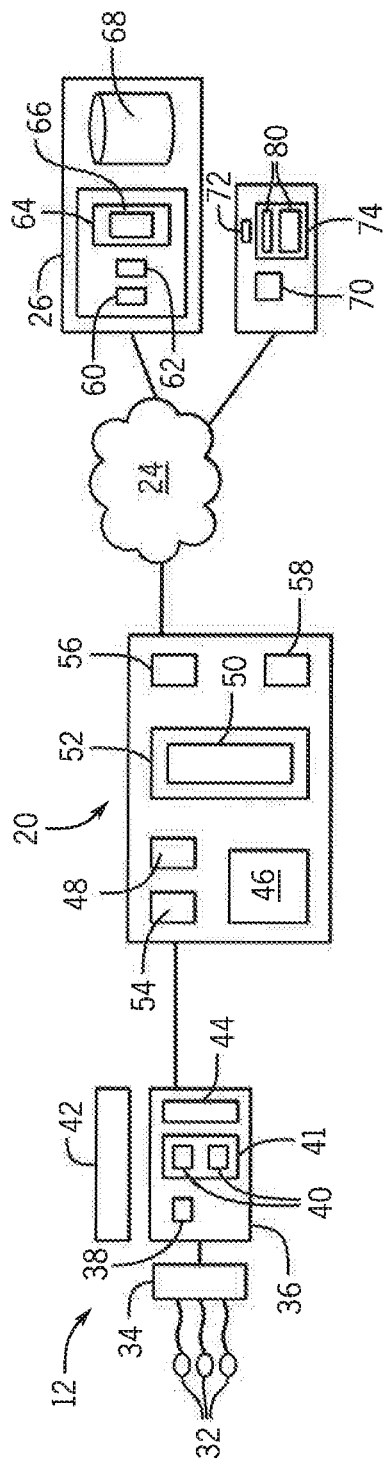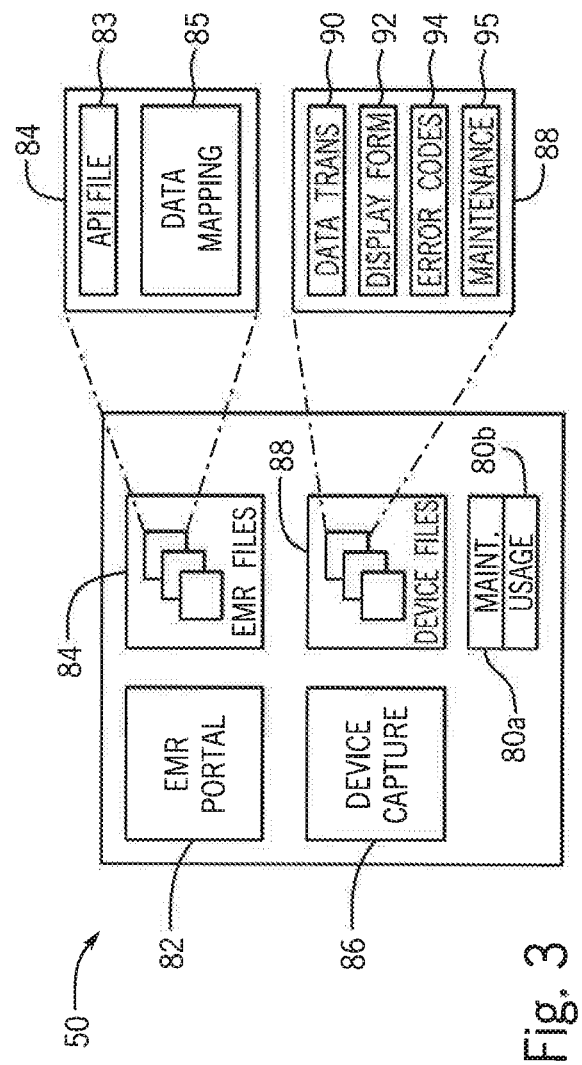

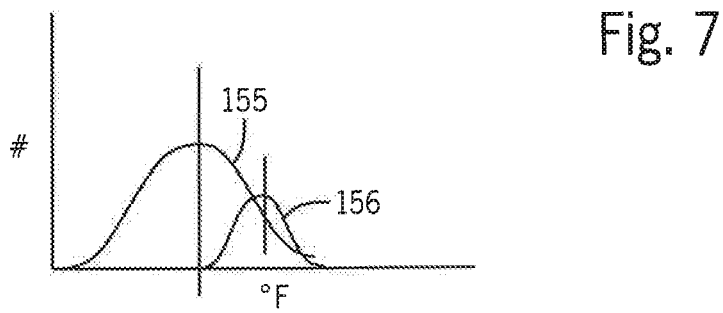
Fig. 5
Fig. 7
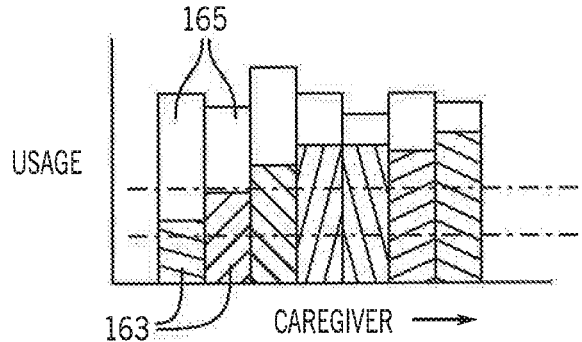
Fig. 8
Fig. 9

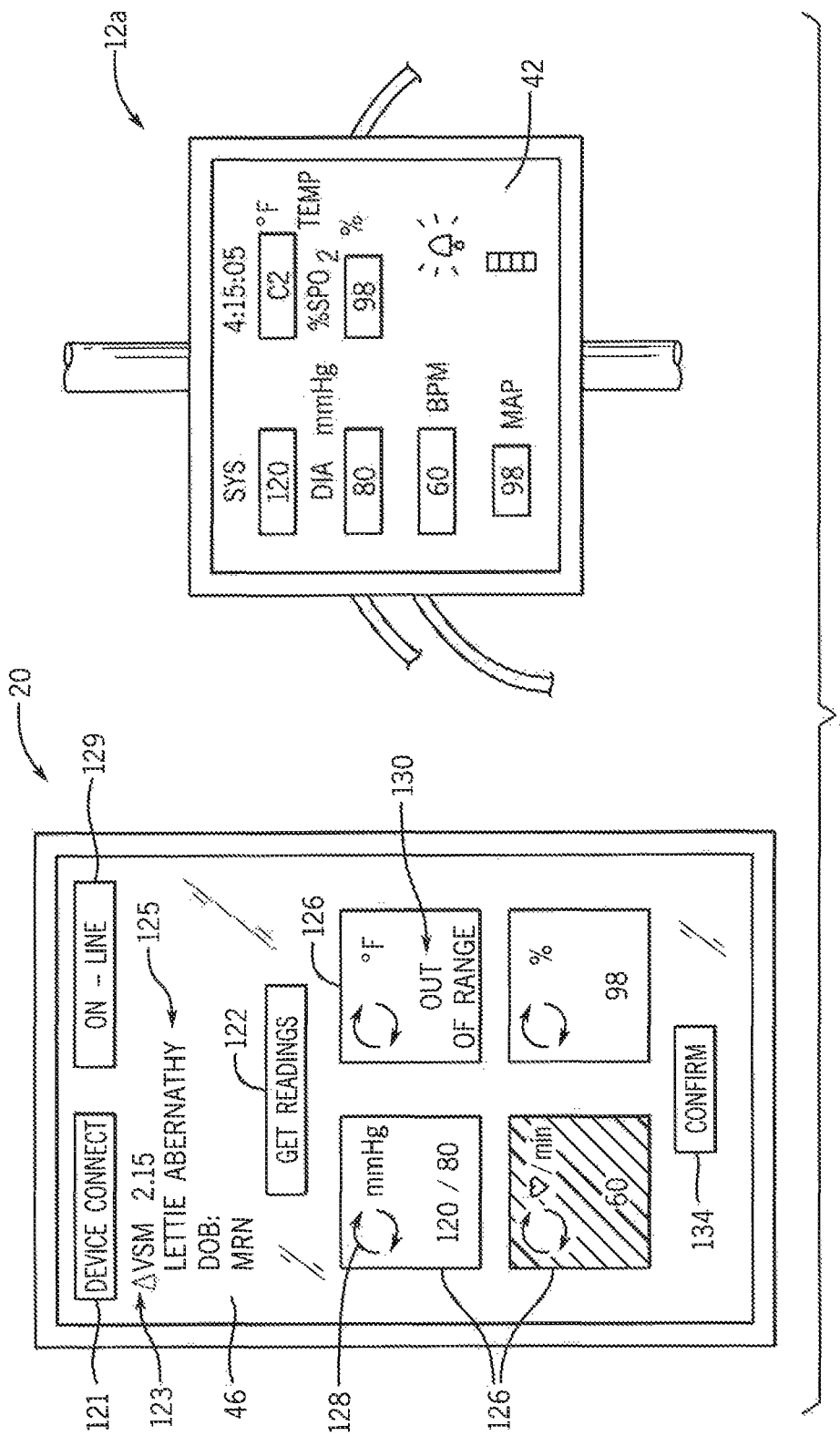

APPARATUS FOR CLINICAL DATA CAPTURE

CROSS REFERENCE TO RELATED APPLICATION

This application claims the benefit of U.S. provisional application 62/697,089 filed Jul. 12, 2018, and hereby incorporated by reference.

STATEMENT REGARDING FEDERALLY SPONSORED RESEARCH OR DEVELOPMENT

Background of the Invention

The present invention relates to patient monitoring devices and in particular to a system for capturing patient data from patient monitoring devices for storage in an electronic medical record with reduced transcription errors.

Electronic medical records (EMRs) are an important development in health care, providing improved accessibility of clinical patient information for a variety of healthcare workers associated with a particular patient and promising improved healthcare monitoring and assessment by providing machine searchable and readable data.

Increasingly, important clinical patient information is collected by automatic patient monitoring devices including, for example, vital signs monitors monitoring patient temperature, blood oxygen, pulse rate, and blood pressure, scales monitoring a patient's weight, and specialized equipment including EKG machines and devices such as ultrasonic bladder scanners for characterizing heart rhythms and urine retention, respectively.

Despite the automatic nature of these machines, the data collected by such patient monitoring devices is often entered into the EMR by hand, that is, with a healthcare provider reading values from the particular patient monitoring device and typing these values into the patient's electronic medical record at a terminal running the EMR program interface. This indirect data entry can cause transcription errors or even lost data, particularly when the EMR terminal is removed from the patient's bedside and the healthcare provider attempts to remember or jots the necessary data down on a slip of paper for later entry.

The need for manual data entry is driven in part by the variety of different patient monitoring devices and electronic medical record systems from different manufacturers that exist in a typical healthcare environment. Even when all of the patient monitoring devices provide for automatic data transmission, configuring this transmission requires that the healthcare provider identify the patient to each different patient monitoring device connected to the patient and provide a mechanism for ensuring that the data is actually transmitted. A fully automatic system where each patient monitoring device is connected to the EMR directly is hampered by the difficulty of configuring such a network and maintaining the network against inevitable outages and corruptions.

SUMMARY OF THE INVENTION

The present invention greatly simplifies the direct transmission of data from patient monitoring devices to an electronic medical record system through the use of a clinical data interface device that that is tightly integrated with the EMR and provides "personality" files allowing it to work with patient monitoring devices from different manufacturers. Tight integration with the EMR allows one-step identification of the patient using actual EMR data so that entry of patient identification for each patient monitoring device can be avoided. The personality files allow the interface device to capture, display, and transmit data between patient monitoring devices and electronic medical record systems from a variety of different manufacturers with otherwise incompatible data storage and transmission protocols.

The personality files may also abstract the clinical data received from each patient monitoring device to provide a consistent visual interface on the clinical data interface device to the healthcare provider as he or she moves among different patient monitoring devices having the same function but different proprietary screens. In one embodiment, the connection of the patient monitoring devices to the clinical data interface device for electronic data transfer can also be used opportunistically to collect patient monitoring device maintenance data, this monitoring data also translated by the personality files.

In this way, the clinical data interface device makes clinical data capture simple and practical for real world healthcare environments without extensive network configuration in an environment likely to include products from a variety of different manufacturers.

Specifically then, the present invention provides a clinical data interface device having a graphic interface outputting a display of data to a user and receiving input of data from a user and a wireless transceiver for receiving wireless signals from a clinical monitor monitoring physiological parameters of the patient and for transmitting wireless signals to a remote electronic medical record database system holding multiple records associated with patients. The clinical data interface device further includes an electronic processor and associated memory, the memory holding non-transitory personality files and at least one non-transitory program executed by the electronic processor to: (a) present a user with an EMR search screen for identifying a record of the remote electronic medical record database system associated with a particular patient; (b) receive data from the electronic medical record database related to the patient; (c) receive data identifying a particular patient monitoring device physically associated with the patient; (d) select a personality file according to the identified particular patient monitoring device and matching the remote medical electronic record database; and (e) receive from the data input physiological parameters and use the selected personality file to perform at least one of selecting and formatting the received physiological parameters for transmission to the electronic medical record database through the wireless transceiver and displaying of the physiological parameters on the graphic interface.

It is thus a feature of at least one embodiment of the invention to provide a system allowing integration of multiple patient monitors using proprietary data communication formats and displays within the EMR. A set of personality files provides the necessary translation of proprietary formats into the common standard required by the EMR and can provide relief from the visual clutter of multiple display interfaces by providing a unified display interface for the healthcare provider. By working directly with the EMR and EMR data, the risk of improper patient identification, modification of the wrong record, or record fragmentation is greatly reduced and direct data logging is encouraged.

The program may use the selected personality file for selecting and formatting the received physiological parameters for transmission to the EMR.

It is thus a feature of at least one embodiment of the invention to provide a system that can practically work in a healthcare environment where different patient monitoring devices are likely to have different manufacturers using different proprietary data storage and communication protocols and encoding. It is another feature of at least one embodiment of the invention to allow the healthcare provider to select freely among different manufacturers to obtain the best patient monitoring devices without concern for compatibility. It is a goal of at least one embodiment of the invention to correctly identify different types of data to particular fields in the EMR record without the need for human intervention based on the type of patient monitoring device and regardless of variations in manufacturing encoding.

The personality file may use the selected personality file for selecting and formatting the received physiological parameters for display on the clinical data interface device.

It is thus a feature of at least one embodiment of the invention to present the healthcare provider with a standardized data screen regardless of proprietary variations in screen formats of different manufacturers, thus improving healthcare provider efficiency in the oversight of the data.

The personality file may further provide translations of error codes from a particular clinical monitor into text messages common to different error codes from different clinical monitors.

It is thus a feature of at least one embodiment of the invention to simplify and standardize error codes among different manufacturers allowing the caregiver to better understand potential problems and their solutions in the demanding healthcare environment.

The clinical data interface device may further repeat steps (d)-(e) using different personality files for different clinical monitors.

It is thus a feature of at least one embodiment of the invention to permit the caregiver to work seamlessly with equipment connected to a given patient or different patients and manufactured by a variety of different companies without the need employ manual data collection and entry into the EMR.

The search screen may display a patient name, a patient identification number, and patient physiological data from the EMR.

It is thus a feature of at least one embodiment of the invention to provide meaningful EMR functionality in the interface permitting robust identification of the patient and review of current recorded clinical data for that patient that may be relevant at the time of data collection and without the need to log onto the EMR terminal.

The clinical data interface may further include a near field communication system, and the data identifying a particular patient monitoring device may identify the particular patient monitoring device using the near field communication system, wherein the near field communication system is selected from the group consisting of an optical tag reader and a radiofrequency identification tag reader.

The clinical data interface device may further receive identification of a healthcare provider for logging into the EMR search screen, and the data received from the EMR by the clinical monitor through the EMR search screen may be limited to data related to patients under the care of the identified healthcare provider.

It is thus a feature of at least one embodiment of the invention to reduce exposure of the EMR data unnecessarily and the possibility of data entry to the wrong patient record as well as to provide a logging of healthcare provider attribution.

The program further receives input from the user to select a subset of the physiological parameters less than all of the physiological parameters for transmission to the electronic medical record.

It is thus a feature of at least one embodiment of the invention to permit the healthcare provider to provide coarse editing of the data (for example, eliminating clearly erroneous or missing data) while still encouraging direct data transmission without human error.

In this regard, the program may prevent modification of the physiological data received from the patient monitoring device either completely or only with marking of that data as modified.

It is thus a feature of at least one embodiment of the invention to discourage human transcription of clinical data such as can introduce significant errors.

The clinical data interface device may tag the data sent to the EMR as being from the clinical data interface device. This data may be used to generate reports indicating usage of the clinical data interface device for sending data to the EMR.

It is thus a feature of at least one embodiment of the invention to provide usage data indicating whether manual transcription has occurred to encourage healthcare providers to use the interface rather than manual transcription.

In one embodiment, the clinical data interface device may receive data identifying a patient and a clinical monitor associated with the patient. This data may be used to receive both wireless signals from the clinical data interface device providing physiological parameters of the patient and display the physiological parameters and wireless signals from the clinical monitor providing maintenance data on the clinical monitor. The physiological parameters may be passed to an electronic medical record for entry into the electronic medical record database for the identified record while the maintenance data may be passed to a maintenance database.

It is thus a feature of at least one embodiment of the invention to provide combined clinical data logging and maintenance data logging without the need for a complex inter-device network among machines from different manufacturers or manual polling of each device by service personnel moving through a healthcare facility.

The clinical monitor may further use the identification of the clinical monitor to select a personality file for that monitor interpreting maintenance data into a common format for storage in the maintenance database.

It is thus a feature of at least one embodiment of the invention to provide a system that can work with a variety of different manufacturer products to compile a centralized maintenance database.

The program may further operate to generate reports indicating required scheduled maintenance based on the maintenance database and may also provide measures of calibration based on statistical analysis of multiple devices working with multiple patients.

It is thus a feature of at least one embodiment of the invention to provide more efficient and improved maintenance diagnostics by longitudinal data analysis of many devices in patients.

These particular objects and advantages may apply to only some embodiments falling within the claims and thus do not define the scope of the invention.

BRIEF DESCRIPTION OF THE DRAWINGS

FIG. 2 is a simplified block diagram of a patient monitoring device, a clinical data interface device of the present invention, and an EMR and HIPAA compliant server of FIG. 1;

FIG. 3 is a function diagram of programs and files used by the clinical data interface device of FIGS. 1 and 2;

FIG. 5 is a screenshot showing a logical arrangement and display of data from an EMR as displayed on the clinical data interface device;

FIG. 6 is screen depictions of the clinical data interface device and the patient monitoring device showing formatting of the data for easy comparison;

FIG. 7 is a logical diagram of a maintenance database compiled by the present invention;

FIG. 8 is a statistical representation of data collected by the maintenance database used for detecting calibration issues; and FIG. 9 is an example usage report generated by the present invention to encourage direct data logging without manual intervention.

DETAILED DESCRIPTION OF THE PREFERRED EMBODIMENT

Figure 1:
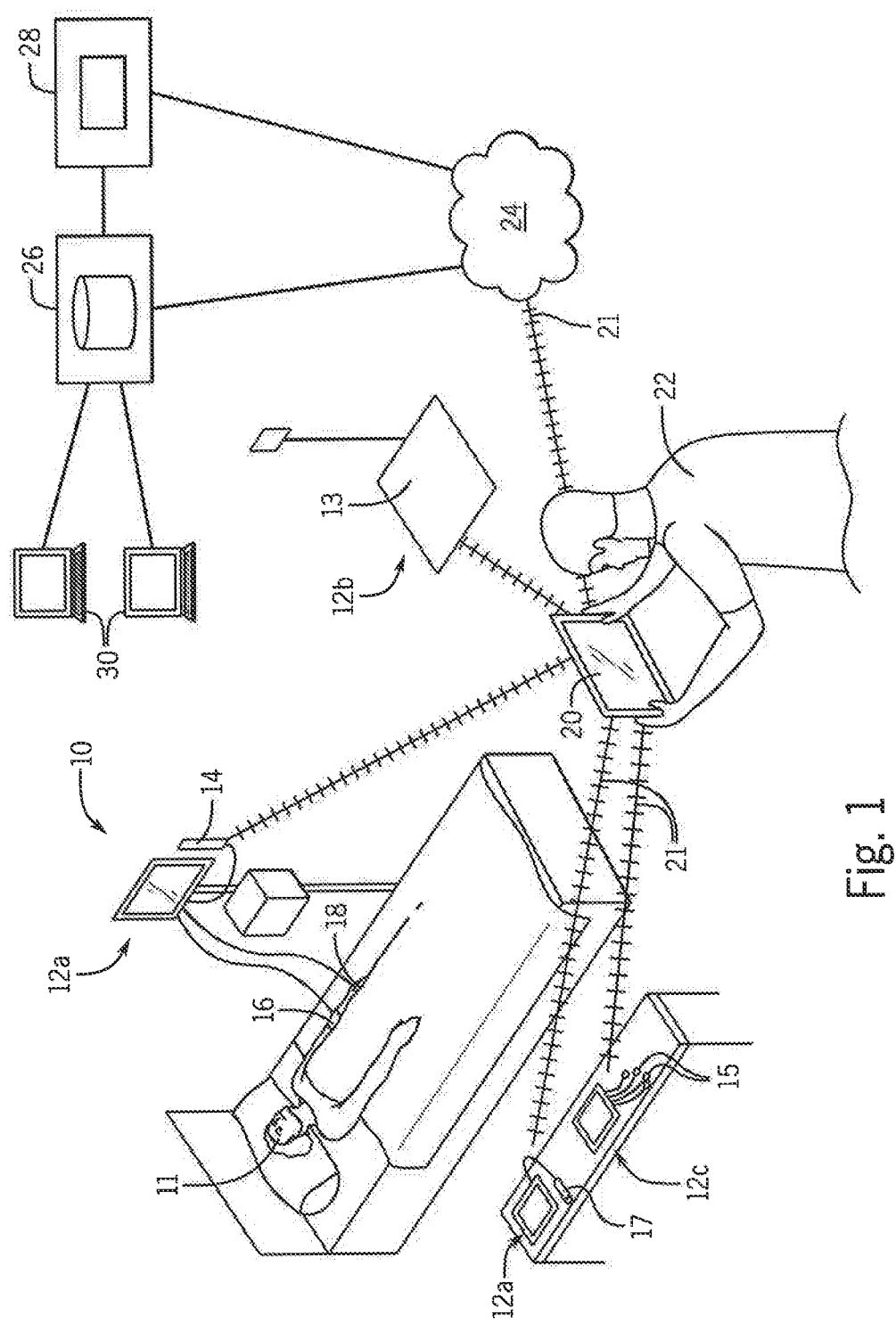
FIG. 1 is a perspective representation of an example healthcare environment showing multiple patient monitoring devices such as may provide local transmission of patient physiological data to a clinical data interface (CDI) device for retransmission to an electronic medical record system (EMR) or HIPAA compliant server.

Referring now to FIG. 1, a healthcare environment 10, such as a hospital or long-term care facility, may provide a variety of patient monitoring devices 12 from different manufacturers for monitoring a given patient 11.

Example patient monitoring devices 12 include: a vital signs monitor 12a providing a connected electronic thermometer 14 (e.g., tympanic or oral) for measuring patient temperature, a blood pressure cuff 16 fir measuring patient blood pressure, and an oximeter probe 18 for detecting pulse rate and blood oxygen. A weighing scale 12b may be provided having a pressure pad 13 with connected load cells for weighing of a patient. Other examples include an EKG machine 12c allowing for the acquisition of EKG data through a variety of electrodes 15 and analysis of that data, and other similar devices such as a bladder scanner 12d providing ultrasonic measure of urinary retention using ultrasound probe 17.

Such patient monitoring devices 12 may provide for data communication with other devices wirelessly, for example, using Bluetooth or other well-known protocols or by wired connection through the use of cabling, for example, using USB or ethernet protocols.

The present invention provides a clinical data interface (CDI) device 20 that may receive data directly from each of the patient monitoring devices 12 without manual transcription of the data. That is, the data may be transferred from the patient monitoring device 12 to the CDI device 20 without human intervention and in particular without the need for a caregiver 22 to read data from the patient monitoring device 12 and enter that data through a keypad or the like into the CDI device 20.

After the CDI device 20 receives the data, under the supervision of the caregiver 22, the CDI device 20 may communicate wirelessly, for example, using Wi-Fi (standard or medical band), with the Internet 24 to transfer the data to a remote electronic medical record system 26 (EMR) either directly or through a HIPPA-compliant server 28. Generally login to the EMR 26 by the CDI device 20 may be done with direct communication between the CDI device 20 and the EMR 26 where the CDI device 20 is used to enter the necessary log on information. After that, communication between the CDI device 20 and the EMR 26 is conducted through an encrypted channel between the CDI device 20 and the HIPPA-compliant server 28.

Generally this path of communication through the CDI device 20 provides a number of benefits including: (1) the ability to work with patient monitoring devices 12 that cannot connect to the Internet 24; (2) the ability to provide encryption of that data for patient monitoring devices that do not provide encryption; (3) a method of avoiding the need to accommodate multiple encryption and/or communication standards when the patient monitoring devices 12 do not provide encryption; and (4) the ability to avoid the need to configure a complex network of multiple patient monitoring devices.

As is understood in the art, the EMR 26 may provide for the storage and access of medical data of the patients 11 to a variety of standard computer terminals 30 for use by other healthcare providers than the caregiver 22. In this regard, and as is generally understood in the art, EMR 26 comprises a specialized database executing on one or more processors for storing clinical medical information about patients collected by healthcare professionals and subject to HIPAA confidentiality requirements. Access to the EMR 26 requires a secure login by a preidentified caregiver 22 to ensure confidentiality, but within that group of authorized individuals, allows ready, centralized access by a variety of healthcare professionals to a single source of patient data eliminating synchronization or fragmentation problems.

The EMR 26 will normally provide database functionality including searching, filtering, and the like of patient records by a variety of fields. The records are normally indexed to unique patient identifiers often including the patient's name and a unique patient identification number. Other confirming information such as height, weight, sex, age, and the like stored in the EMR 26 may also operate to uniquely identify the patient as well as provide clinical value. More generally, the EMR 26 may provide all data necessary for clinical treatment of a patient 11 including not only data collected from the patient monitoring devices 12 and similar clinical data required for clinical practice but also physician notes, patient prescriptions, prognoses, test results, diagnostic images, appointment schedules, and attending healthcare provider names. Normally this data is recorded in fields of the record which provide context for the data. The logical arrangement of an EMR 26 will be discussed further below with respect to FIG. 5.

Example EMR systems (sometimes also termed electronic health record (EHR)) suitable for use with the present invention are commercially available through a variety of manufacturers including: PointClick Care having a place of business in Mississauga, Canada, and providing an EMR under the designation Core EHR platform; MatrixCare having a place of business in Minnesota, United States; and Netsmart having a place of business in New York, United States, and providing an EMR under the tradename HealthMedx.

Referring now also to FIG. 2, each of the patient monitoring devices 12 will generally be manufactured by different companies and employ different software and data storage conventions. Nevertheless, they will typically provide a core set of common features including one or more physiological sensors 32, in this example being the thermometer 14, blood pressure cuff 16, finger cuff 18, pressure pad 13, electrodes 15, or ultrasound probe 17 discussed above. A hardware interface 34 is provided to preprocess data from these sensors 32 and to digitize that data for communication of this data to a processing system 36. The processing system 36 may include an electronic processor 38 operating to execute one or more programs 40 stored in electronic memory 41. The electronic processor 38 may also communicate with a user display interface 42, typically a touchscreen or display screen plus membrane switch combination, and may provide for a data port 44 for communicating with other electronic devices, for example, through Bluetooth and/or a wired USB or ethernet connection.

In the present embodiment, the CDI device 20 may make use of a specially programmed and configured tablet computer having a touchscreen 46 communicating with a processor 48 executing an interface program 50 stored in the electronic memory of the processor 48. The CDI device 20 may receive data from the patient monitoring devices 12 through local port 54, for example, being a Bluetooth and/or USB port and may provide a connection to the Internet 24, for example, through a transceiver 56 of the type well known in the art, for example, employing Wi-Fi standard. Ideally the CDI device 20 is compact to move with the caregiver 22 as he or she visits multiple different patients 11 and therefore has a self-contained battery power source 58 with sufficient capacity to operate the CDI device 20 during the day without other electrical connection. Alternatively, a CDI device 20 may be associated with particular patient monitoring devices 12 on a permanent basis.

Hardware suitable for the CDI device 20 includes but is not limited to tablet computers commercially available from Apple Inc. of California, USA, under the tradename of iPad, and comparable devices.

The EMR 26 discussed above may reside on a standard computer server including a port 60 for communication with the Internet, as well as one or more processors 62 communicating with the port 60 and with a memory 64 holding an EMR database program 66. The processors 62 may also communicate with a mass storage device 68 holding the database of patient records.

The HIPPA-compliant server 28 may likewise provide a port 70 for communication with the Internet 24 and a processor 72 communicating with that port 70 and communicating with electronic memory 74 holding additional portions of the interface program 50 whose operation will be discussed below. In addition, the HIPPA-compliant server 28 may store in the electronic memory 74 auxiliary data 80 from which reports on utilization and equipment maintenance may be prepared as will be discussed below.

Referring now to FIGS. 2 and 3, generally the interface program 50 as will be described may be flexibly allocated to either or both of the CDI device 20 or HIPPA-compliant server 28. This interface program 50 includes an EMR portal component 82 providing basic access to the EMR 26 including patient look up, outputting of essential patient biographical and medical data including patient name, patient identification number (e.g., medical record number (MRN)), date of birth, and the like, as well as selected clinical data about the patient including, for example, the stored data of the type collected by the various patient monitoring devices 12.

The EMR portal component 82 may also receive data for entry into the EMR 26 at a particular patient record. The EMR portal component 82 uses the EMR database program 66 executed by the EMR 26 or more typically will be a separate program using the API (application programmers interface) of the EMR 26 to duplicate some essential functions.

In this respect, the EMR portal component 82 may allow identification of only patients associated with a particular caregiver 22 and/or only patients associated with a given facility for that caregiver when the caregiver 22 works with multiple facilities, and may include a login routine for allowing that caregiver 22 to log into the EMR 26 while preventing access by other unauthorized individuals. For a given caregiver 22 only selected information for the patient may be provided according to the caregiver's responsibility, and the entry of data into the EMR 26 may be similarly controlled. For example, a physician caregiver 22 may have access to all of the EMR 26 and data entry capabilities for all data fields of the EMR 26 while a healthcare assistant may be limited to a few fields of the EMR 26.

The EMR portal component 82 may communicate with an EMR personality file 84 providing information about the protocols 83 for communicating with a particular EMR 26. In this way the CDI device 20 and/or HIPPA-compliant server 28 may operate with a variety of different types of EMRs 26 having different proprietary data storage approaches simply by changing the personality file 84. Generally the personality file 84 identifies characteristics unique to the EMR 26, for example, how particular data fields are identified or stored within the database of the EMR 26, For this purpose, the personality file 84 may include a data mapping table 85 mapping a given type of data (identified generically) to its representation in the EMR 26 and indicating any extra data required by the EMR 26. For example, most EMRs 26 provide a field for specific blood oxygen but some EMRs 26 may also require additional observations by the caregiver 22 with respect to the entered data, for example, an annotation indicating whether the patient is on supplementary oxygen. Similarly, data for patient temperature may be annotated with respect to the type of thermometer in use. This data mapping information may be used to properly enroll data from the patient monitoring device 12 in the EMR 26 and to provide instructions to the caregiver 22 about additional information that may be required. The personality file 84 may also describe the communication protocol needed to read and write from the EMR 26.

The interface program 50 may also include the device capture portion 86 which controls the capture of data from a variety of different types of patient monitoring devices 12. The device capture portion 86 also includes a set of device personality files 88 (analogous to the EMR personality files 84), Each of these device personality files 88 will be related to a particular type and brand of patient monitoring device 12 and may include a data translation table 90 linking encoded data from the particular patient monitoring device 12 to the generic type of data that can be used to match this data with an entry in the data mapping table 85 for correct introduction to the EMR 26. The data translation table 90 may also provide information about the communication protocol necessary for the particular patient monitoring device 12, for example, commands necessary to cause the device to transmit certain information.

The device personality files 88 also include a device format file 92 which controls the arrangement and format of data (also identified to a generic label in common with those described above) presented on the touchscreen 46 of the CDI device 20 according to the type of patient monitoring device 12 so as to present a standard interface to the caregiver 22 for a given type of patient monitoring device regardless of the manufacturer. Generally the format of this display on the touchscreen 46 will be such as to extract only portions of the data displayed on the particular patient monitoring device 12 as may be desired by the data capturing process. When only a single type of patient monitoring device 12 from a single manufacturer is used in the healthcare environment 10, the formatting of the touchscreen 46 may closely follow the formatting of the patient monitoring device 12 with respect to arrangement of the data to assist the caregiver in double checking that data.

The device personality files 88 may also include error code translation tables 94 which convert error codes for each specific type of patient monitoring device 12 into a standard English-language explanation of those errors as will be discussed below. The error translation tables 94 may map functionally similar error codes from patient monitoring devices 12 to identical text descriptions providing the same freedom from unnecessary diversity in the description of this type of data. The device personality files 88 may also provide a protocol file 95 for accessing device maintenance information from the patient monitoring device, for example, cumulative operating time and the like as will be discussed below. Such protocols typically vary among different manufacturers but may be translated into a common format for the generation of a unified report as will be discussed below.

Finally the interface program 50 may also provide for the storage of auxiliary data 80a and 80b providing maintenance and utilization data as will be discussed below.

Figure 4:
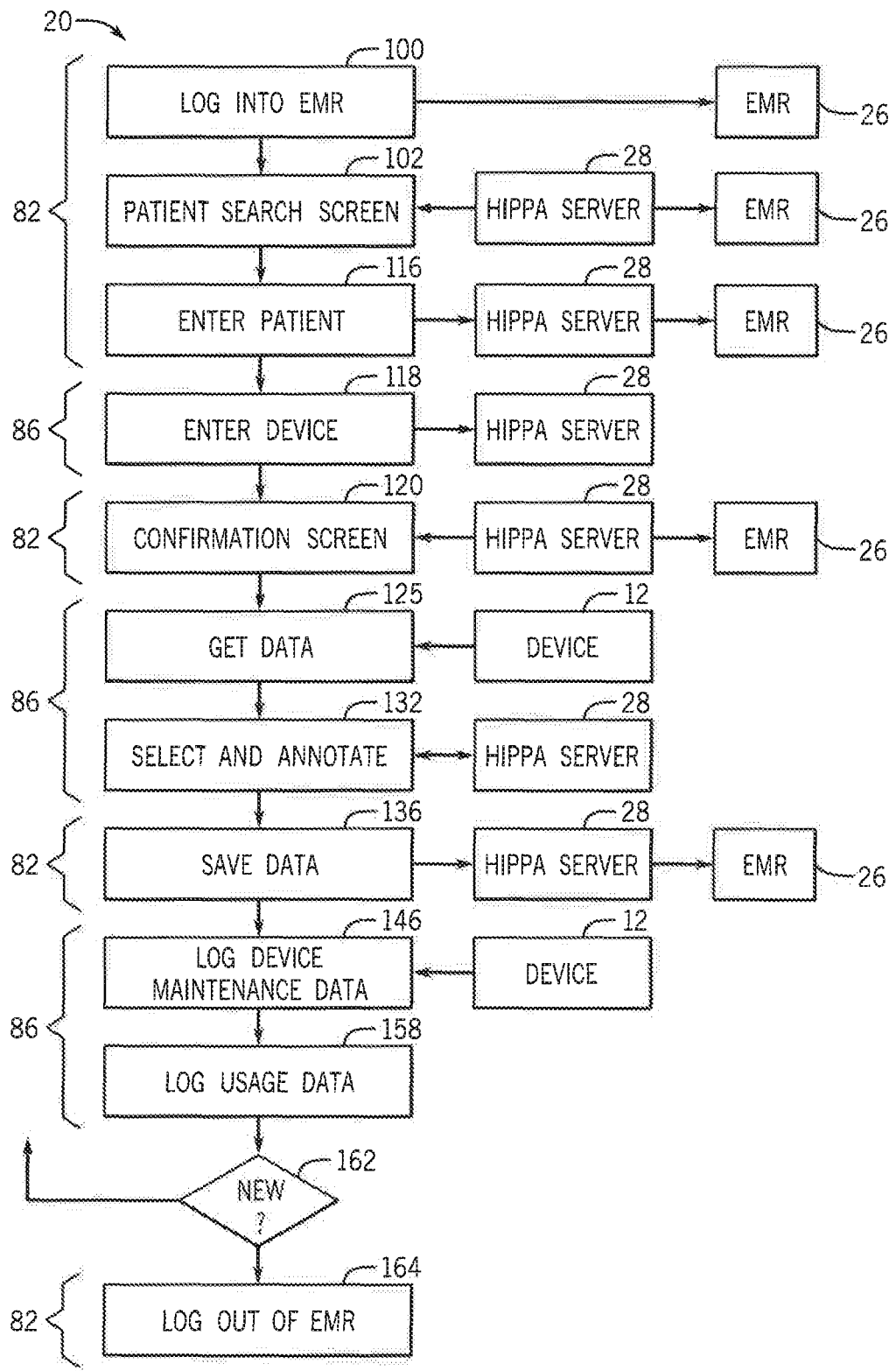
FIG. 4 is a flowchart showing the operation of the programs of FIG. 3.

Referring now to FIGS. 3 and 4, the interface program 50 begins by using the EMR portal component 82 to prompt the caregiver 22 to log into the EMR 26 per process Nock 100. This process uses password authentication information native to the EMR 26 and provides direct communication with the EMR 26 through the Internet 24. Based on the caregiver's information which also links the caregiver 22 to a particular set of patients 11 held in the EMR 26, the EMR 26 communicates through the HIPPA-compliant server 28 back to the CDT device 20 to provide a simplified EMR search screen per process block 102.

Referring momentarily to FIG. 5, the search screen 104, which may be displayed on the touchscreen 46 of the CDT device 20, will desirably provide for basic search tools for sorting and filtering a set of patient records 106 of the EMR 26 each associated with a different patient 11 associated with the caregiver 22. The search screen 104, responding to a query from the caregiver 22, may display various fields of the patient record including: the patient name 108, date of birth 110 (and other personally identifying information), medical record number 112, as well as selected clinical information of the type to be captured, for example, blood pressure information 114 and other information to be collected by the various patient monitoring devices 12. Basic EMR functionality is provided for further filtering and sorting this display information according to any of the data fields displayed; however, manual entry or editing of the display data may be either prohibited, or prohibited to a particular class of employees (for example, nurses but not certified medical assistance (CNA) or geriatric nursing assistant (GNA)). Other methods may be used to discourage such manual entry including marking that data as edited manually.

Referring again to FIG. 4, using the search screen 104, the caregiver 22 may search for and identify a particular patient associated with clinical information to be gathered from the patient monitoring devices 12 as indicated by process block 116 again communicating this information through the HIPPA-compliant server 28 to the EMR 26. Generally the data from the EMR 26 may be used to positively identify the patient 11, and the caregiver 22 may be asked to confirm this matching, for example, through a pop-up screen as discussed below.

At process block 118, a particular patient monitoring device 12 is identified, for example, by selecting from a list of local wireless devices or by connecting a cable. The particular patient monitoring device must be positively identified by a near field technique to prevent possible wireless connections to devices in adjacent rooms or the like. For example, a serial number affixed to the housing of the patient monitoring device 12 may be matched to a list of devices forming potential Bluetooth pairing partners automatically presented by the CDI device 20. The caregiver 22 may simply select among those devices per process block 118 or use other entry methods to confirm the particular patient monitoring device 12, for example, using scanning of barcodes or the reading of an RFID tag and the like affixed to the patient monitoring device 12. Generally these near field techniques will be limited to operation at less than 3 m and ideally less than 1 m.

This information about the particular patient monitoring device 12 is communicated to the interface program 50 and serves to inform interface program 50 with respect to the selection of the correct device file 88 for automatic data transfer.

Referring also to FIG. 6, at succeeding process block 120 of FIG. 4, the identified patient 11 and patient monitoring device 12 are displayed on the CDI device 20 display touchscreen 46 so that the caregiver 22 may confirm this information. The touchscreen 46 further indicates that the device (patient monitoring device 12) is detected by message 121 and provides the serial number 123 of that patient monitoring device 12 for visual matching and confirms that the CDI device 20 is communicating online by message 129 with either the EMR 26 or the HIPPA-compliant server 28. The name, date of birth, and medical record number 127 of the patient 11 are also provided.

At this time the caregiver 22 may press the "GET READINGS" button 122 presented on the touchscreen 46 to upload current data from a patient monitoring device 12 (shown as vital signs monitor 12a in FIG. 6) per process block 125 of FIG. 4. This data is transferred wirelessly or through a wired connection from the patient monitoring device 12 to the CDI device 20 using the appropriate personality files 88. Depending on the particular patient monitoring device 12, the received data is displayed on the CDI device 20 in a standard format for that type of device, in this case providing multiple display squares 126 each associated with a different data type. As noted above, all vital signs monitors 12a (regardless of manufacturer) may provide a similar display on the CDI device 20 simplifying the task of reviewing this data by the caregiver 22. In the special case when all patient monitoring devices 12 of a particular type have the same display configuration (for example, being from the same manufacturer), the display of the display squares 126 on the CDI device 20 will mimic the same layout as on the display interface 42 of the patient monitoring device 12. For example, the CDI device 20 may show the blood pressure readings in the upper left-hand corner on the touchscreen 46 mimicking the display interface 42 on the patient monitoring device 12. Again, this simplifies a visual checking that the data has been properly transferred from the patient monitoring device 12 to the CDI device 20.

The data as received is all labeled, for example, with its units (e.g., millimeters of mercury, degrees Fahrenheit, etc.) on the touchscreen 46. Individual data elements represented by each display square 126 may be updated by pressing a refresh symbol 128 in the corner of each display square 126 causing a fresh uploading of that data from the patient monitoring device 12. In cases where the desired data (for example, temperature in this figure) indicates an error condition (e.g., C2), this error condition is translated into an English-language message 130 using the error code translation tables 94 discussed with respect to FIG. 3. Data that is not relevant to the EMR but displayed on the display interface 42 of the patient monitoring device 12 may be blocked from display on the touchscreen 46 of the CDI device 20 according to the personality file 88 again simplifying the caregiver's task in confirming the correct data has been transferred.

As indicated by process block 132, the caregiver may then select particular data elements represented by display squares 126 to be transferred to the EMR 26 by affirmatively selecting or deselecting a particular display square 126 by tapping it once, an action which can be undone by another tap. The status of the display square 126 as selected or deselected may be indicated by dimming or "graying" out the features of unselected display squares. Only "ungrayed" or selected data will be transferred from the CDI device 20 to the EMR 26. At this time, the caregiver 22 may also modify the values of any particular display square 126, for example, by pressing and holding the display square 126, to allow modification of the data of the data square 126, for example, by a pop up keyboard (not shown). This may be necessary in the case of equipment malfunction (including loss of wireless connections or network connections) or recognized inaccuracy, but it results in the marking of the data recorded in the EMR 26 (which normally comes from the CDI device 20) with a "modified" flag indicating that this data was not taken without modification from the CDI device 20. The personality file 88 may include permissible physiological ranges for each of the data values of each of the display squares 126 to provide an error condition to the user when a manually entered value exceeds these range limits and prevent entry of erroneous data into the patient file.

The caregiver 22 may then press a confirm button 134 which brings up a summary of the selected data (not shown) and may request additional information needed by the EMR 26 for any particular piece of selected data. For example, the pulse rate information may bring up a menu offering a set of choices adding supplemental information about whether the measured pulse rate was "regular," "irregular with new onset," "chronically irregular," "irregular unable to determine onset," or "unable to determine" or "not applicable." The need for this information and the population of the menu may be derived from the EMR personality file 84 obtained in the interface program 50, for example, from data stored in the CDI device 20 or in the HIPPA-compliant server 28.

At process block 136, once the data for transfer is selected and annotated, the caregiver 22 may press a button (not shown) to send this data to the EMR 26 via the HIPPA-compliant server 28. The data as sent may make use of the EMR portal component 82 discussed above so that it is correctly enrolled in the database of the EMR 26 for the patient whose record was identified earlier. In one embodiment, this data is time stamped at the time of receipt by the CDI device 20 to prevent the transmission of stale data. All data transmitted from the CDI device 20 is indicated to be from the CDI device 20 so that usage data can be collected as discussed below with respect to FIG. 9.

Referring now again to FIGS. 4 and 7, the present invention uses the regular data collection provided by the caregiver 22 associated with his or her rounds to also monitor the patient monitoring devices 12 with respect to maintenance items per logging block 140. Per process block 140, the API file 95 may be accessed to communicate with the patient monitoring device 12 to cause it to upload operating data of that patient monitoring device 12 for storage in the auxiliary data 80a shown in FIG. 7. Such data may identify the particular patient monitoring device 12 by serial number 142, its total operating hours 144, as well as component operating hours 146 (for example, inflation cuff cycles for blood pressure measurement) when those items have different maintenance schedules. Other diagnostic information, for example, component failures or system error codes, may also be uploaded.

The auxiliary data 80a may provide a field derived from the personality files 90 indicating the service limit 150 of each patient monitoring device 12 or its components to trigger automatic warning messages, for example, sent by e-mail from the HIPPA-compliant server 28 to identified administrative personnel. When the CDI device 20 or similar device is used by maintenance personnel, the auxiliary data 80a may further record the last service of the patient monitoring device 12 in field 152 and the maintenance person's identity per field 154.

Auxiliary data 80a may be mined to collect service information to predict service requirements and may also be used to identify calibration issues or other trending of particular patient monitoring devices 12.

Referring momentarily to FIG. 8 the auxiliary data 80a may be used to detect calibration errors, for example, by comparing data statistics for a variety of patient monitoring devices 12 comparing a first distribution 155 to a similar distribution collected for particular patient monitoring device 12 indicated by distribution 156 to see if there is a general biasing that would suggest the need for calibration.

Referring again to FIG. 4, the CDI device 20 may also log usage of the CDI device 20 for caregivers 22 identified per process block 100 to provide usage data monitoring. For example, a number of operations of process block 136 may be recorded as indicated by process block 158 and auxiliary data 80b. This auxiliary data 80b may show total usage of the CDI device 20 for logging data or may show, as indicated, relative amounts of data logging directly using CDI device 20 indicated by bar 163 versus data logged manually indicated by bar 165. This usage data 80b may be used to generate a report, for example, as indicated in FIG. 9, ranking caregivers according to usage of the CDI device to identify particular caregivers that may benefit from encouragement or training to better utilize the features of the CDI device 20. This auxiliary data 80b may alternatively be used to identify particular patient monitoring devices 12 that are difficult to use or patient monitoring devices 12 that are difficult to use with the CDI device 20 such as may suggest a modification of the interface screens or the like.

At decision block 162, the caregiver 22 may select a new patient monitoring device 12 and return to process block 118 without the need to return to process block 102 (so long as the new patient monitoring device 12 is associated with the same patient 11) minimizing the need for repeated logging into the EMR 26 or selection of patient. Generally these processes will continue until the caregiver logs out per process block 164.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to an "EMR", "clinical data interface," "a processor" or the like should be understood to include one or more computer systems operating alone or interconnected to provide a distributed environment(s) operating as a logical entity, configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A clinical data interface device comprising:
   a portable unit adapted for relocation among different patient locations by a user and including:
   a graphic interface having an electronic display and electronic sensor responsive to user commands and adapted to output a display of data to a user and receive input of data from a user;
   a data input being a wireless or wired circuit adapted to communicate with a patient monitoring device monitoring physiological parameters of the patient to receive physiological parameters from the patient monitoring device;
   a wireless transceiver being an electronic circuit adapted to communicate with a remote electronic medical record database system (EMR) holding multiple records associated with patients; and
   at least one electronic processor and associated memory, the memory holding at least one non-transitory program executed by the at least one electronic processor to:
   (a) present the user with an EMR search screen for accessing a record of the remote electronic medical record database system associated with a patient at the patient location;
   (b) provide the user with access to the record of the remote electronic medical record database system;
   (c) receive data from the accessed record of the electronic medical record database related to the patient;
   (d) receive an input from the user confirming that a particular patient monitoring device is physically associated with the patient and the accessed record;
   (e) identify a personality file from among multiple personality files according to the physically associated patient monitoring device; and
   (f) receive from the data input, physiological parameters having a first electronic communication format
   (g) use the identified personality file to determine that the physiological parameters should be formatted to a second electronic communication format;
   (h) format the physiological parameters to the second electronic communication format;
   (i) transmit the physiological parameters to the accessed record of the electronic medical record database in the second electronic communication format through the wireless transceiver and
   (i) display the physiological parameters on the graphic interface.

2. The clinical data interface device of claim 1 wherein the at least one non-transitory program uses the identified personality file for selecting and formatting the received physiological parameters for transmission to the EMR.

3. The clinical data interface device of claim 2 wherein the identified personality file is selected from among different personality files associated with different patient monitoring devices providing given physiological information provide different formatting to be given physiological information to produce identically formatted data for transmission to the electronic medical record system.

4. The clinical data interface device of claim 1 wherein the at least one non-transitory program uses the identified personality file for selecting and formatting the received physiological parameters for display on the clinical data interface device.

5. The clinical data interface device of claim 4 wherein the identified personality file is selected from among different personality files associated with different patient monitoring devices providing given physiological parameters and providing different formatting to produce a same visual appearance of the given physiological parameters on the display of the clinical data interface device when the clinical data interface device is used with the different patient monitoring devices providing the given physiological parameters.

6. The clinical data interface device of claim 2 wherein the identified personality file further provides translations of error codes from a particular patient monitoring device into text messages common to different error codes from different patient monitoring devices.

7. The clinical data interface device of claim 2 wherein the non-transitory program executed by the at least one electronic processor further repeats steps (d)-(e) using different identified personality files for different patient monitoring devices.

8. The clinical data interface device of claim 1 wherein the EMR search screen displays a patient name, a patient identification number, and patient identifying data from the EMR.

9. The clinical data interface device of claim 1 further including a near field communication system communicating with the patient monitoring devices to identify at one patient monitoring device to the user, wherein the near field communication system is selected from the group consisting of an optical tag reader and a radiofrequency identification tag reader.

10. The clinical data interface device of claim 1 wherein the at least one non-transitory program further receives identification of a healthcare provider for logging into the EMR search screen and wherein the data received from the EMR by the patient monitoring device through the EMR search screen is limited to data related to patients under the care of the identified healthcare provider.

11. The clinical data interface device of claim 10 wherein the data transmitted to the electronic medical record database is linked to the identification of the healthcare provider.

12. The clinical data interface device of claim 1 wherein the data input is selected from the group consisting of a wireless communication port and a wire cable port.

13. The clinical data interface device of claim 1 wherein the at least one non-transitory program further receives input from the user to select a subset of the physiological parameters less than all of the physiological parameters received from the particular patient monitoring device for transmission to the accessed record.

14. The clinical data interface device of claim 1 wherein the at least one non-transitory program permits modification of the physiological data received from the patient monitoring device while marking that data as modified.

15. The clinical data interface device of claim 1 wherein the at least one non-transitory program tags the data sent to the EMR as being from an identified clinical data interface device.

16. The clinical data interface device of claim 1 wherein the at least one non-transitory program further operates to generate reports indicating usage of the clinical data interface device for sending data to the EMR.

17. The clinical data interface device of claim 1 wherein the at least one non-transitory program further operates to download personality files through the wireless transceiver.

18. The clinical data interface device of claim 1 wherein the at least one non-transitory program identifies the personality file by communicating with a remote device holding multiple personality files.

19. The clinical data interface device of claim 1 wherein the identified personality file includes a first component associated with the remote electronic medical record database system and mapping a type of data to its representation in the remote electronic medical record database system and a second component associated with the particular patient monitoring device linking data from the particular patient monitoring device with the type of data, so that together the first and second components provide a mapping of data from the particular patient monitoring device to its representation in the remote electronic medical record database system.

20. The clinical data interface device of claim 19 wherein second component is received by the clinical data interface device from a remote device.

21. The clinical data interface device of claim 4 wherein the identified personality file provides a formatting to produce a representation of the physiological parameters on the display of the clinical data interface device having a layout matching a display of the confirmed patient monitoring device.

22. The clinical data interface device of claim 1 wherein the program executed by the at least one electronic processor responds to the input from the user, confirming that a particular patient monitoring device is physically associated with the patient, to transmit the physiological parameters in the second electronic communication format to the accessed record of the electronic medical record database through the wireless transceiver or receive data from the data input for display on the graphic interface.

* * * * *